United States Patent
Lietzau

(10) Patent No.: US 11,964,031 B2
(45) Date of Patent: Apr. 23, 2024

(54) ROOT CANAL FILLING COMPOSITION

(71) Applicant: Markus Lietzau, Berlin (DE)

(72) Inventor: Markus Lietzau, Berlin (DE)

(*) Notice: Subject to any disclaimer, the term of this patent is extended or adjusted under 35 U.S.C. 154(b) by 510 days.

(21) Appl. No.: 16/956,012

(22) PCT Filed: Dec. 19, 2018

(86) PCT No.: PCT/EP2018/085981
§ 371 (c)(1),
(2) Date: Jun. 19, 2020

(87) PCT Pub. No.: WO2019/122009
PCT Pub. Date: Jun. 27, 2019

(65) Prior Publication Data
US 2021/0085571 A1 Mar. 25, 2021

(30) Foreign Application Priority Data

Dec. 22, 2017 (DE) .................... 10 2017 131 135.1
Dec. 22, 2017 (DE) .................... 20 2017 107 865.5
Dec. 22, 2017 (EP) .................................. 17210071

(51) Int. Cl.
*A61K 6/77* (2020.01)
*A61C 5/50* (2017.01)
*A61K 6/54* (2020.01)
*A61K 6/60* (2020.01)

(52) U.S. Cl.
CPC ............... *A61K 6/77* (2020.01); *A61C 5/50* (2017.02); *A61K 6/54* (2020.01); *A61K 6/60* (2020.01)

(58) Field of Classification Search
CPC ....................................................... A61K 6/54
See application file for complete search history.

(56) References Cited

U.S. PATENT DOCUMENTS

| 5,385,469 A | 1/1995 | Weissman |
| 2003/0148247 A1* | 8/2003 | Sicurelli, Jr. .......... A61C 13/30 |
| | | 433/224 |
| 2005/0066854 A1 | 3/2005 | Jia |

FOREIGN PATENT DOCUMENTS

| EP | 0644743 A1 | 3/1995 |
| WO | 0067659 A1 | 11/2000 |
| WO | 2013128952 A1 | 9/2013 |
| WO | 2014115090 A1 | 7/2014 |

OTHER PUBLICATIONS

International Preliminary Report on Patentability and Written Opinion of the ISA, dated Jun. 23, 2020 in International Patent Application No. PCT/EP2018/085981.
International Search Report dated Mar. 15, 2019 in International Patent Application No. PCT/EP2018/085981.

* cited by examiner

*Primary Examiner* — Michael F Pepitone
(74) *Attorney, Agent, or Firm* — Wood, Phillips, Katz, Clark & Mortimer

(57) ABSTRACT

A root canal filling composition for placement in a tooth root canal, a kit for providing the required materials, and a method for applying the materials. The root canal filling composition comprises a glass-fibre post and a dentine-adhesive filling material.

22 Claims, 2 Drawing Sheets

ROOT CANAL FILLING COMPOSITION

BACKGROUND OF THE INVENTION

Field Of The Invention

The invention relates to a root canal filling composition for placement in a tooth root canal, a kit for providing the required materials, and a method for applying the materials.

BACKGROUND ART

The material of choice for bacteria-proof sealing of the root canal system in teeth is currently gutta-percha, with sealers based on zinc oxide-eugenol, calcium hydroxide, silicone or epoxy resin. The gutta-percha/sealer system fulfils, to a large extent, all the requirements that have to be met by a root canal filling material, such as biocompatibility, chemical stability, homogeneity, radiopacity, low technique-related sensitivity, and the possibility of revision. However, gutta-percha does not allow a completely bacteria-proof sealing of the root canal system. Bacterial penetration can occur along the dentine-sealer or sealer-gutta-percha interfaces, since gutta-percha is neither compatible with the root canal dentine nor forms a bond with the sealer.

In endodontics, adhesive sealers are therefore gaining popularity over conventional sealers. A hybridisation between collagen (root canal dentine) and plastic (sealers based on methacrylate) on the one hand should enable a bacteria-proof sealing of the root canal system, and on the other hand—as in coronal cavities—an increase in mechanical resistance through the adhesive bond is being discussed. In contrast to coronal dentine, however, parameters such as anatomical features of root canal dentine, the polymerisation shrinkage of the sealer, and the high C-factor (ratio of bonded to unbonded surface area) in the root canal may impair the integrity of the adhesive bond to the root canal dentine and promote infection.

A further problem of adhesive root canal fillings made of plastics-based sealer/gutta-percha, and thus a possible entry point for bacteria, is constituted by the lack of a chemical bond between the plastics-based sealer and the polyisoprene component of gutta-percha.

Currently, there are two strategies for adhesive root canal filling. One strategy, to bind methacrylate-based sealers to gutta-percha, makes use of the coating of conventional gutta-percha peaks with plastics components (polybutadiene diisocyanate methacrylate). In the coating (10 to 15 μm), the bonding of the polyisoprene of the gutta-percha to the methacrylate in the sealer is mediated by a bifunctional diisocyanate which, on the one hand, bonds to the polyisoprene of the gutta-percha via a hydrophobic group and, on the other hand, mediates the bond to the sealer via a hydrophilic methacrylate group. Even without the use of a primer, the hydrophilic sealer causes a pronounced formation of tags in the dental canaliculi and a hybrid layer.

A second approach involves creating a filled, thermoplastic composite as an obturation material, which is similar to gutta-percha in its properties. The incorporation of methacrylates ensures the connection to the methacrylate-based sealer. Resilon is a synthetic root canal filling material consisting of polycaprolactone (polyester polymer), dimethacrylates, as well as glass and radiopaque fillers. Resilon is soft and thermoplastic, similarly to gutta-percha. The plastics-based material is available either in the form of pens or pellets and can be used with the known obturation techniques. After preparation of the root canal system, Resilon is adhesively bonded to the root canal dentine using a self-etching primer and a dual-curing, methacrylate-based, hydrophilic sealer to coronally stabilise the structure. However, long-term studies have shown that Resilon increasingly leaks due to changes in its physical properties, resulting in the formation of cavities and channels in the filling or between the filling and the tooth substance, which promote the colonisation of germs.

However, contact of endodontic sealers with the periapical hard and soft tissues may lead to local or even systemic reactions (Geurtsen 2001). In plastics-based sealers, the ingredients may have a cytotoxic or mutagenic effect.

SUMMARY OF THE INVENTION

The invention now addresses the problem of overcoming the problems encountered in the prior art and in particular aims to provide a bacteria-proof root canal filling which does not have the known side effects of the composites or sealers.

The problem is solved by a root canal filling composition and a method and kit for its production, having the features of the independent claims.

Thus, a first aspect of the invention relates to a root canal filling composition for placement in a tooth root canal. The root canal filling composition according to the invention, hereinafter also referred to as a composition or root filling, comprises a glass-fibre post with a first and a second end, wherein an apical stop made of a physiological material is arranged at the first end and the glass-fibre post, at least in some regions, is surrounded over its entire surface by a filling material. According to the invention, the filling material comprises or consists of a dentine-adhesive filling material.

The advantage of the composition according to the invention is that a bacteria-proof root canal filling can be offered, which is also absolutely compatible with the surrounding tissue. This is achieved by the combination of physiological apical stop and dentine-adhesive seal.

In this case, a physiological material is understood to be one that has no or only very slight, short-term harmful effects on living tissue, the focus in the present case lying particularly on the tissue adjacent to the apex, i.e. fundamentally the periodontium. The apical stop forms a barrier between living tissue and filling material and thus prevents contact and a chemical or physiological interaction between filling material and tissue. In addition, the stop prevents filling material from escaping from the apex into the surrounding tissue. The arrangement of the apical stop thus prevents short-term and long-term damage to the periodontium when combined with dentine-adhesive filling material. Therefore, the composition according to the invention can also be used for root canal filling in the case of inflamed apices or bone lesions in the apical region.

The expression "fully enclosed in some regions" in this case means a region of the glass-fibre post starting from the first end, which comprises the filling material over its entire circumference. The limitation "in some regions" refers to the length of the glass-fibre post and clarifies that no filling material is arranged in a region adjacent to the second end, in particular to enable handling of the glass-fibre post. In particular, starting from the apical stop from the first end, the filling material is arranged over the entire surface over a length of the glass-fibre post in the range of from 85% to 99.9% of the canal length, in particular in the range of from 90% to 99% of the canal length, or over a length in the range of from 5 mm to 23 mm, in particular in the range of from 8 mm to 19 mm.

The dentine-adhesive filling material is a material that penetrates and seals the dental canaliculi of the tooth in the uncured state due to adhesive interactions. This results in a bacteria-proof seal in two ways. Firstly, no germs can enter the tooth root from outside via the dentinal tubules. Secondly, the formation of a gap between dentine and filling material is prevented, so that, here too, no germs from the oral cavity or from the apical region can penetrate such a gap. Since bacteria need food and space to multiply, the germs have no basis for reproduction. The composition according to the invention therefore offers a significant reduction of medium- and long-term complications, since on the one hand inflammation processes that can be triggered by the dentine-adhesive material are prevented (short- to medium-term complications) and on the other hand a new colonisation of bacteria in remaining free spaces (medium- to long-term complications) can be prevented.

A dentine-adhesive luting is a treatment method used in dentistry to attach filling material or dentures to the tooth. The dentine surface of a cavity is chemically pre-treated by allowing low-viscosity dentine bonding agents to penetrate the surface structures and, after chemical curing, to form a micromechanical bond between dentine and a composite filling. As a result, it is possible to avoid macromechanical retentions, which result in a greater loss of tooth substance.

In addition, the prevention of gap formation between dentine and filling material leads to a stabilisation of the tooth and prevents increased brittleness.

Composites (Latin compositum 'compound') are tooth-coloured plastic filling materials for dental treatment. Colloquially, the materials used since the 1960s are often also referred to as plastic fillings. The dental applications of composites are fillings above the root canal and the attachment of ceramic restorations, crowns and root posts.

Composites consist of an organic plastics matrix, which is mixed with inorganic fillers. Initially, the composites were used almost exclusively in the anterior region. In the meantime, composites with an increased filler content have also been used in the posterior region. The further development of bonding agents and the dentine-adhesive technique has enabled this use in the posterior region.

Modifications of the composites, which shall also be understood in the present case to be included under the term 'composite', are compomers, ormocers and glass ionomer cements. The latter formally belong to a different class of materials and comprise the above-mentioned materials in part.

The processing of composite-based filling material, i.e. a material which, based on volume, consists mainly of composite, is more complex and time-consuming compared to an amalgam filling, because it is applied in a number of layers and is cured layer-by-layer with a polymerisation lamp to reduce the polymerisation shrinkage of the material. A prerequisite for a permanently tight composite filling is the adhesive attachment to the tooth. This is achieved, for example, by etching, especially with phosphoric acid, and by then applying an adhesive.

The matrix of composites consists in particular of methacrylate-based plastics. In addition, traces of formaldehyde, glutaraldehyde and acids may also be contained.

Preferably, the filling material comprises fillers, which may reduce or even prevent shrinkage of the material. Glass, ceramic and quartz particles (silicates, sands) are used as fillers. These are further preferably coated with silanes, which improve their bonding with the plastic. In other words, silanisation serves as a bonding phase between the organic and inorganic matrix. Silanes are able to chemically bind glass to an organic matrix. On the one hand, the silanol groups of the silane enter into a condensation reaction with the glass surface of the fillers. On the other hand, a covalent bonding between the methacrylic acid group of the silane and the matrix plastic of the organic phase takes place.

The fillers are referred to as the inorganic phase of the composites. In the present case, fillers are selected from: glass or glass ceramics (for example barium-aluminium-glass), silicates, silicon dioxide.

The organic phase of composites is advantageously a methacrylate (acrylic), which is especially light-cured. Hydroxyethyl methacrylate (HEMA), triethylene glycol dimethacrylate (TEGDMA) or bisphenol glycidyl methacrylate (BisGMA) are used.

In addition to the actual monomer as the main component of the organic phase, composites such as BisGMA composites are preferred, which also contain other, in particular functional components. The other components should be selected from the group: mono-, di- and triacrylates (as comonomers)—see: Copolymer, camphorquinone or phenylpropanediol (as initiator of photopolymerisation after illumination with the blue light of a polymerisation lamp), toluidine (as accelerator of photopolymerisation), hydroquinone (as inhibitor of photopolymerisation so that this does not start already by normal daylight), benzophenone (as UV stabiliser so that the plastic filling remains colour-stable in the patient's mouth over the years), dyes and pigments (for colouring the plastic filling).

In a preferred embodiment, the filling material comprises composites selected from the group: highly viscous, pluggable composites—high filler content; low-viscosity, flowable composites—reduced filler content—as an intermediate layer among the pluggable composites. The polymerisation of the composite is preferably carried out chemically and/or by light.

Dual-curing composites (i.e. both light- and chemically polymerisable composites) are used when the supply of light to the composite material is partially excluded and are therefore particularly preferred for use in the composition according to the invention. These are then, for example, only (additionally) cured with light at the accessible edges, since the deeper layers are not accessible to light, while chemical polymerisation takes place at the points inaccessible to light.

It is advantageous if the filling material comprises a composite, in particular a chemically curing, dual-curing or light-curing composite.

Another advantage of the composite is that it is a self-adhesive composite. This reduces on the one hand the number of components of the composition and on the other hand the treatment time when inserting the composition into a tooth, since at least the application of what is known as a primer and possibly preparatory etching can be spared.

In a preferred configuration of the invention it is provided that the glass-fibre post is formed in one or more parts. In the present case, a multi-part configuration means that a plurality of elongate parts which are not connected to one another in an integrally bonded manner and are arranged next to one another form the glass-fibre post. The individual parts are preferably detachably connected to a support, for example a ring or a cap which runs around the circumference of the glass-fibre post. Of course, a one-part glass-fibre post also comprises a plurality of fibres, which are then, however, connected to each other in an integrally bonded manner. The advantage of a one-part post is in particular the uncomplicated handling. By contrast, a multi-part glass-fibre post is characterised by increased flexibility, greater variability in thickness, by the removal or combining of individual parts, and better adaptability to tapering root canals. For example, only some of the parts are pushed into the tip of a tapering root canal, while the others only start at a height where the root canal is wider. This is not possible for simple one-part posts. This disadvantage is advantageously compensated for by a tapering tip of the first end of a one-piece glass-fibre post, although a flexible adaptation to various root canal geometries, as is provided with multi-part posts, cannot be achieved.

Dual-curing composites still have a very high residual monomer content of up to 45% after curing. This is suspected to result in side effects for the patient. In order to counteract these, in a further configuration of the invention, the glass-fibre post is at least in some regions, especially in a region adjacent to the apical stop, designed in such a way that it allows light to escape laterally. When the composition is illuminated after it has been placed in the tooth, a part of the light is introduced into the glass-fibre post at the second end and transmitted through it to the first end. Also on a conventional glass-fibre post, the light emerges at this end. The nature of the glass-fibre post such that it additionally allows light to escape laterally means that a larger area, especially an area inside the root canal, is accessible to light. The degree of polymerisation is significantly increased and a monomer content is reduced. In addition, composites that are predominantly light-cured can also be used.

Nevertheless, the configuration according to the invention makes it possible to ensure that the composite material has no contact with living tissue of the patient, neither apically nor laterally.

A design of this kind of the glass-fibre post is preferably achieved by roughening the glass-fibre post in the relevant region and/or by having regular or irregular elevations and depressions, for example in the form of a honeycomb or box pattern. Such configurations may lead to a reduction in stability in the glass-fibre post, but this can be compensated for by bonding the composite. In addition, stability can be increased if only some of the parts of a multi-part glass-fibre post have this feature.

Alternatively or additionally, the fibres of a multi-part glass-fibre post are embodied with different lengths, with the individual parts being flush at the first end. At the second end, light is then output at different heights at the various ends of the glass fibres. This results in a wider range for light output and a larger light-cured surface. This configuration allows an increased light output area without reducing the stability of the post.

In a further preferred configuration of the invention, it is provided that the apical stop comprises or consists of a bioresorbable material. This has the advantage that a maximum physiological compatibility is provided.

This is particularly advantageous if the apical stop comprises a biocompatible tissue or bone adhesive. This not only avoids irritation of the surrounding tissue, but the composition according to the invention, when applied in a root canal, even heals bone lesions in the apical region of the periodontium, or at least supports the healing thereof.

The apical stop particularly preferably comprises alginates, collagens, a hyaluronic acid composition, as well as medical tissue adhesives such as cyanoacrylates, calcium phosphates, in particular hydroxyapatite, polylactones, in particular poly-caprolactones such as poly(glycolic acid-co-caprolactone or poly(L-lactide-co-caprolactone) polylactides, such as poly(L-lactide-co-DL-lactide) and poly(DL-lactide-co-glycolide), acylacrylonitrile, dialkylmethylene manolate, α-substituted vinylidene alkylsulphonates, sulphonates, oligo-p-dioxanone and/or derivatives thereof.

In the group of cyanoacrylates, especially alkyl cyanoacrylates, preferably with an alkyl chain length in the range of from 1 to 12, particularly preferably with a chain length in the range of from 2 to 8, are preferred for use as apical stops. They have the advantage that they cure completely with mild bases, such as water, which is always present when used according to the invention, without further polymerisation initiators. The additional application of heat and/or light for curing is not necessary. When using cyanoacrylates, the properties of the apical stop are adjustable by their alkyl chain length. With increasing chain length, the compatibility and hardness of the adhesive as well as its curing time increase.

Cyanoacrylates for use according to the invention as an apical stop are advantageously mixed with electron-rich olefins, such as 4-methoxystyrene, in order to (co-)polymerise therewith during curing.

The apical stop advantageously comprises functional additives in addition to the hardenable materials mentioned. These functional additives preferably include stabilisers, thickening agents, binders, polymerisation inhibitors such as sulphur dioxide, nitrogen oxide, O-sulphur benzoic anhydride and/or phosphorus pentoxide and/or plasticisers.

Alternatively or in addition, the apical stop additionally comprises inorganic nanoparticles, for example those consisting of or comprising $SiO_2$ or APOSS (acrylate polyhedral oligomeric silsesquioxane). Their addition is suitable to further improve the cell compatibility of the apical stop.

It is further preferred if the apical stop is pre-formed or is present as a precursor in pasty, that is to say only partially hardened form. Curing is then carried out in particular by light curing by means of the introduction of light via the glass-fibre post and/or by curing of a 2-component mixture. If the stopper is pre-formed, this is understood to be a flexible, in particular compressible plug which, when inserted into the root canal, can be compressed in such a way that it penetrates into the apical region and, if necessary, partially expands again at the destination, thereby sealing the apex.

The apical stop is then inserted until it is constricted, whilst maintaining its complete physiological form.

In a further preferred configuration of the invention, it is provided that the apical stop has a length of not more than 1/10, in particular not more than 1/20, preferably not more than 1/30 of the length of the glass-fibre post. This results in the apical stop, after insertion into the root canal, reaching into less than 1/10, in particular less than 1/15, preferably not more than 1/20 of the root canal. This corresponds substantially to the working length, i.e. +/−0, although preferably even −0.5 to −1 mm is achieved with over-tamping. This has the advantage that the largest possible part of the root canal is filled with the dentine-adhesive filling material, thus closing as many dentinal tubules as possible and stabilising the tooth over its entire length and not leaving any cavities or unstable regions in which compressible or resorbable material is arranged, which would indirectly lead to cavities and thus instabilities and/or bacterial colonisation.

Another aspect of the invention relates to a kit for producing the root canal filling composition according to the invention. The kit according to the invention comprises a glass-fibre post, in particular in one of the configurations described above as a prosthetic high stabilisation and anchor for the covering filling, an apical stop, preferably in one of the configurations described above or a precursor thereof, and a dentine-adhesive filling material in one of the configurations described above or precursor thereof.

The kit according to the invention advantageously makes it possible to produce the root canal composition described above with all the advantages described there. The presentation as a kit also has the advantage that all the necessary starting materials and tools are included, so that only the kit according to the invention has to be provided when performing a tooth root canal filling, and individual substances do not have to be looked for in a time-consuming search. Furthermore, all starting materials are always consumed and ordered at the same time. All this leads to a particularly effective time management for the treating dentist. In addition, there are planning and synergy advantages on the producer's side, which in turn makes it possible to reduce costs, which is noticeable for both the producer and the treating dentist.

In the present case a precursor is a compound or material that can be chemically or physically converted into the stop or filling material according to the invention, in particular during application. In particular, precursors are understood to be 2-component materials or materials that react chemically in air.

The filling material is pre-mixed and particularly advantageously is not cured or is only partially cured. For this purpose it is ready for application in the predetermined state. To protect against chemical reaction and against bacteria etc., the filling material is sealed airtight and in particular light-tight. In this case, provision in a cannula or syringe is preferred, this having an applicator in particular.

Depending on the material selected, the apical stop is preferably available as a compressible, resilient plug or thread prefabricated in the kit. The size of the plug or the diameter of the thread is in this case in the range of from 0.1 to 8 mm, in particular in the range of from 0.2 to 1.5 mm, preferably in the range of from 0.3 to 1 mm. The size of the plug preferably varies depending on the material used, in particular its compressibility. The use of a collagen plug with a proportion of hydroxyapatite in approximately cubic form with an edge dimension in the range of from 0.3 to 1 mm is particularly preferred.

Alternatively or in addition to the use as an apical stop, depending on the material composition, the kit contains a, in particular, pasty, that is to say viscous composition, which is then brought to the intended apical location by means of a suitable tool, in particular a cannula or a syringe. This is preferably the case when using the aforementioned medical tissue adhesives, such as alkyl cyanoacrylate compositions or precursors thereof.

In a further preferred configuration, the apical stop has an irregular, in particular roughened and/or corrugated surface on at least one side. This side preferably corresponds to a surface which, when used as intended, is directed apically, that is to say a side of the stop facing away from the root canal and facing a periodontium, in particular a bone. This embodiment has the advantage that, when using the composition according to the invention, macrophages may attach themselves better to the surface of the stop and thus may accelerate the healing of bone lesions.

Alternatively, the apical stop is present in the form of a paste and/or in powder form. In particular in the last variant, a premix is made before application.

It should be understood that the kit according to the invention is used in endodontics and in particular not in prosthetics. The kit according to the invention differs from one used in prosthetics in particular by the component of the apical stop.

In contrast to prosthetic posts, significantly thinner glass-fibre posts are used in this case, with a diameter in the region of a root canal in particular in the range of from 0.2 to 0.75 mm, preferably 0.3, 0.45 or 0.6 mm. In other words, the glass-fibre post used does not exceed a diameter of 0.65 mm or 0.3 mm. Anchoring advantageously can be achieved in addition to the root canal filling if the glass-fibre post is longer than the root canal.

Alternatively, the filling material and/or the apical stop is available in individually packaged, non-reactive single starting materials, which are first mixed before application. It is preferable if all starting materials are contained in equivalent quantities in the kit.

In an advantageous embodiment of the kit according to the invention, the kit comprises a dentine-adhesive primer and/or an etchant. The primer is provided in particular if the composite is not a self-adhesive composite.

The etchant is preferably pasty or liquid and is also filled in a tube or syringe with applicator.

In a further preferred embodiment of the invention, the glass-fibre post, the apical stop or its precursor and the dentine-adhesive filling material or its precursor are present in the kit spatially separated from each other, in particular individually packaged.

Alternatively, said constituents are present in the form of the root canal filling composition according to the invention, wherein the filling material arranged on the glass-fibre post is additionally enclosed in an insulated manner in such a way that it is fixed to the glass-fibre post, in particular with contact to the latter, and in particular is sealed hermetically and in a sterile manner. This is possible, for example, by means of a welded-on sheathing, for example in the form of a plastics material. The sheathing is arranged here in such a way that the apical stop is not also covered, but rather is separated from the filling material to ensure that the apical stop is not contaminated with the, possibly, non-physiological filling material. This configuration offers the advantage that the composition is available in a few simple steps with enormous time savings and can be applied directly.

Both configurations offer the advantage that the reactants do not have to be dimensioned or that there are residual stocks that in turn have to be stored. Regardless of the configurations of the kit, it is important to understand that the individual packages within the kit are always hermetically sealed, but in particular sterile.

In the alternative embodiment, it is also advantageous if filling material and/or material of the apical stop is also present separately packed in the kit in order to fill up any free spaces in the root canal after application of the root canal filling.

It is advantageous to have a holder in the form of a cap or an easily detachable ring arranged at the second end of the glass-fibre post.

In a further preferred configuration, the kit includes each of the components in a quantity that allows the filling of exactly one tooth. In principle, the kit may be available in different sizes, with each size being adapted to the requirements of a tooth type. This means in particular that the kit size is advantageously adapted to the number of tooth roots or canals. In the different kit designs, in particular the quantity of composite, apical stops and the size (thickness) and quantity of glass-fibre posts vary.

Alternatively, the kit comprises the individual components in a quantity for a number of applications. This has the advantage, among other things, that the same kit can be used for different teeth (front and back teeth). It is not necessary to stock a number of different kits. Furthermore, a larger scale is more attractive for the consumer from an ecological and economic point of view.

A further aspect of the present invention is a method of applying a root canal filling composition according to the invention, in particular using the kit according to the invention.

In the present case, the root canal filling composition is applied, especially ex-vivo, i.e. for example in an extracted tooth.

In any case, the tooth will have been previously opened beyond the apical area. The method according to the invention comprises the following steps in the order given:

a) First, the apical stop made of the physiological material is inserted into the canal up to the apex. The material is over-tamped, i.e. most of its volume is pressed out of the apex root canal into the surrounding tissue. As a result, the apical stop protrudes from the apical region and does not reach more than $1/10$ of the total root canal length into the root canal.

Then b) the filling is applied. This comprises the glass-fibre post and the dentine-adhesive filling material. For example, the glass-fibre post is dipped into the filling material, or the filling material is applied around it by application. The mixture of post and filling material is then inserted into the canal as far as the apical stop. During this process, the filling material forms a bond with the glass-fibre post. If the post is configured in a number of parts, the post is splayed out by the filling material, and filling material penetrates into the gaps created. This results in a better connection on the one hand, and on the other hand cavities are avoided. In addition, the stabilising effect of the glass-fibre post is increased.

Finally c) the filling material is cured. This is preferably achieved with the aid of light. In order to ensure thorough curing and to keep the proportion of non-polymerised monomers or oligomers small, curing can either be carried out in individual layers, or illumination can be achieved internally by selection of the glass-fibre posts according to the invention. In this case, however, it is necessary that part of the second end of the glass-fibre post of the curing lamp is accessible during curing. A part of the light is then introduced into the glass-fibre post, and from there through it to the first end, where it emerges, especially laterally, and hardens the composite.

Optionally, there is a further step between steps a and b, in particular the step of introducing a self-adhesive bonding agent, especially with the aid of a length-adjusted aid, in particular what is known as a brush.

The method according to the invention has in particular the advantage of saving time, because in comparison to the usual methods, additional greasy trimming of the coronal cavity and a revision of 50 to 70% of the newly placed root canal filling is not necessary and thus a plastics build-up is carried out in only one step. Furthermore, it is used for training purposes to be able to carry out the method for in-vivo application without complications.

The advantage of the application in living systems is that a bacteria-proof root filling is possible for the first time, this not having been possible until now due to the side effects of the composites. The apical stop and especially the small extent thereof in the root canal allows this, as well as a maximum stabilisation of the root by the cured composite compared to the use of a degradable bone adhesive.

When using the kit alternative in which the root canal filling composition is already present in one piece, it is introduced into the root canal with the apical stop first, in such a way that the apical stop closes the canal apically and, in particular, emerges from the root end into the surrounding tissue. The end remaining in the root canal does not extend into it more than $1/10$ of the total canal length.

The working length is measured and observed using means known to a person skilled in the art. This includes, for example, radiographic or electronic measurement, which is then observed with the aid of a scale or stopper on each working tool, especially on the insertion aid of the apical stop or the glass-fibre post.

In the method according to the invention, preference is given in particular to the use of the materials in the embodiments described above. In other words, all of the above subjects and uses of the invention and embodiments thereof shall be combined advantageously. In addition, the comments regarding specific subjects and uses of the invention always also relate to the other subjects and uses and their embodiments.

Further preferred configurations of the invention result from the other features described in the dependent claims.

The various embodiments of the invention mentioned in this application can be combined with each other advantageously, unless otherwise stated in the individual case.

BRIEF DESCRIPTION OF THE DRAWINGS

The invention will be explained below in exemplary embodiments with reference to the associated drawings, in which.

DETAILED DESCRIPTION OF THE PREFERRED EMBODIMENT

Figure 1:
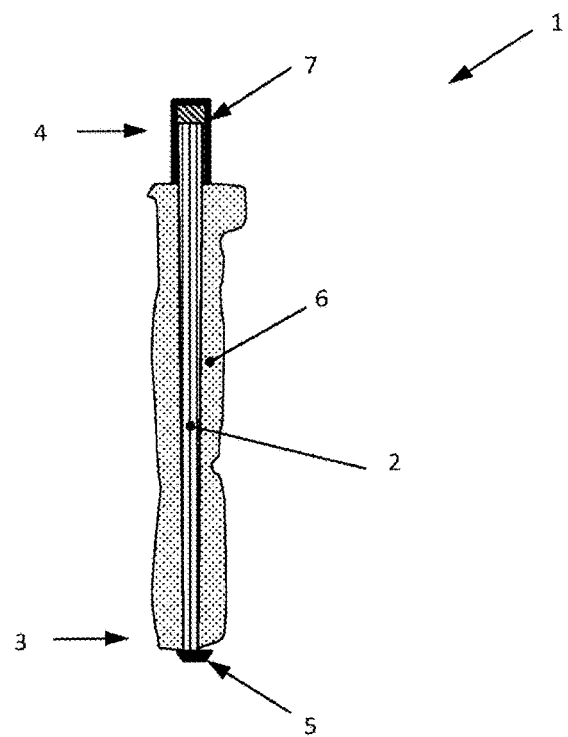
FIG. 1 shows a schematic basic sketch of a root canal filling composition in a preferred configuration.

FIG. 1 shows a schematic basic sketch of a root canal filling composition 1 in a preferred configuration of the invention. Shown is a glass-fibre post 2, which may be configured in one or more parts. The glass-fibre post 2 has a first end 3 and a second end 4. In particular in a multi-part configuration, the glass-fibre post 2 tapers towards the first end 3. An apical stop 5 is located at the first end 3 of the glass-fibre post 2. This is made of a physiological material and preferably comprises a bone adhesive, such as hydroxyapatite and/or an alkyl cyanoacrylate. At the second end 4 of the glass-fibre post 2, there is arranged a holder 7 in the embodiment shown. This holder 7 is, in principle, optional, but allows for stabilisation, especially if the glass-fibre post 2 is configured in a number of parts. A filling material 6 consisting of a dentine-adhesive material is arranged around the glass-fibre post 2. The dentine-adhesive material has the advantage that, when applied in an open tooth root canal, it penetrates the dentinal tubules and thus tightly seals the canal bacteria and gives the open root canal stability again after closing. The filling material 6 may also contain particles which reduce the effect of shrinkage of the filling material 6 and at the same time increase the stability of the filling.

Figure 2:
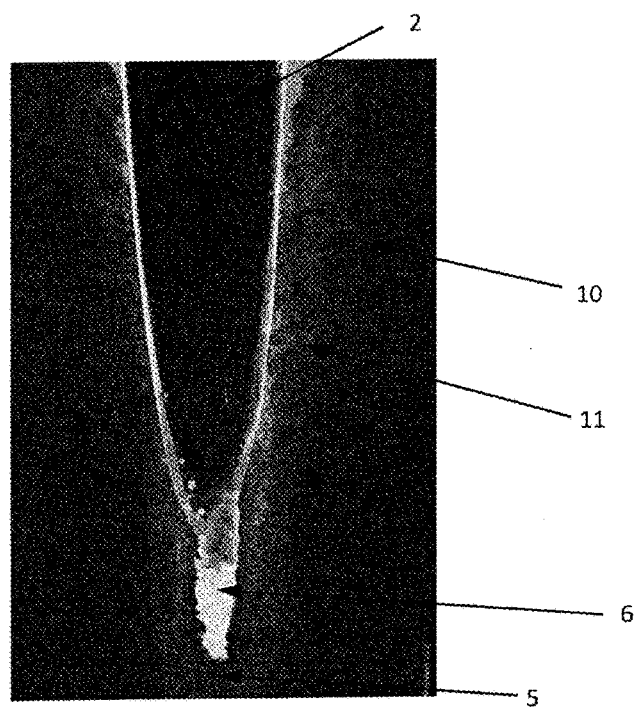
FIG. 2 shows an X-ray image of a root canal filling composition applied in a root canal in the preferred configuration.

FIG. 2 shows a high-resolution X-ray image of a root canal filled with the root canal filling composition 1 according to the invention. In this configuration, the filling material 6 comprises a radiopaque additive which makes it possible to make the arrangement of the filling material in the tooth root canal visible in the X-ray image. Shown is the glass-fibre post 2, which in the embodiment shown runs continuously towards the apical end 3. This is achieved in particular by the multi-part configuration of the glass-fibre post 2, so that several fibres of the glass-fibre post 2 are configured in different lengths so that the diameter of the entire glass-fibre post 2 increases from the apical end 3 to the second end 4 of the glass-fibre post 2. It is clear that the filling material 6 also penetrates into a strongly tapered region of the root canal, which represents the apical region of the tooth root canal, but without coming out of it. Instead, the exit of the apical region towards the periodontium (not shown) is sealed by the apical stop 5. In FIG. 2, the apical stop 5 is only shown as a shadow, as no radiopaque additives are added to it. It is clear, however, that only a very small part of the apical stop 5 extends into the root canal, namely to no more than one tenth, in particular no more than one twentieth of the total root canal length.

Figure 3:
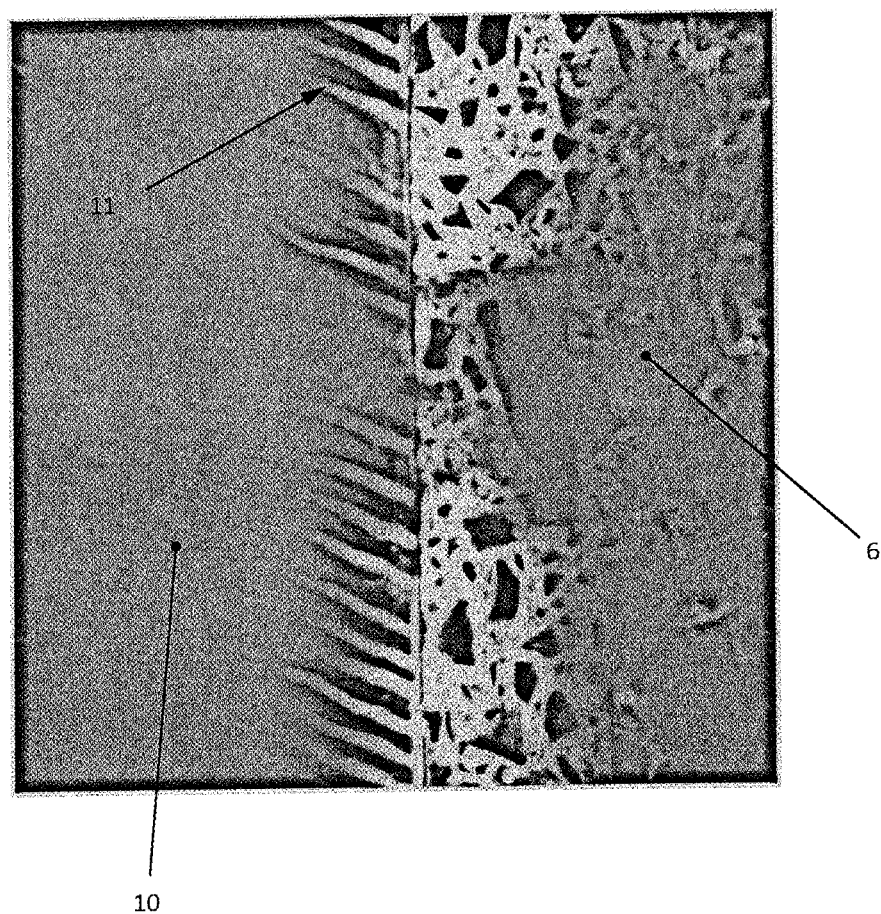
FIG. 3 shows an enlarged view of a detail of the X-ray image from FIG. 2.

FIG. 3 shows a detail of the root canal filling shown in FIG. 2. The adhesion of the filling material to the dentinal tubules 11 of the tooth root canal and also the fillers added to the filling material 6 can be seen particularly clearly.

The root canal filling composition 1 according to the invention and the method for its application enable a bacteria-proof and stable root canal filling.

The following is a practical example for carrying out the method according to the invention in a preferred non-limiting embodiment:

The prerequisite is a prepared and dried channel. Subsequently, the apical stop according to the invention is inserted, followed by a self-etching bonding agent. After a short drying time, the glass-fibre post according to the invention with the filling material arranged on it, especially the composite, is inserted into the prepared and apically closed canal. Finally, after the composite has cured, the tooth is built up in the upper area, and the outer surfaces are modelled in one continuous step, that is to say without relatively long waiting times.

Practical Example

Detailed application of the root canal filling composition according to the invention in a preferred configuration using the kit The individual components were packaged separately from one another. In this example, the kit comprises, in addition to the basic provision of a multi-part glass-fibre post, a 2-component filling material with fillers and physiological stop in the form of a collagen plug comprising hydroxyapatite or a pasty alkyl cyanoacrylate composition, the kit further comprising a bonding agent, in particular a self-adhesive/self-etching bonding agent comprising an etchant in the form of phosphoric acid and a dentine-adhesive primer.

First, an apical stop, for example made of a plug comprising hydroxyapatite or an alkyl cyanoacrylate, is inserted into the root canal and over-tamped using a suitable tool in such a way that the stop remaining in the canal does not extend into the root canal by more than 1/10, in particular not more than 1/20 of the total canal length.

Next, the dentine surface is wetted with a self-adhesive bonding agent.

The monomer, i.e. the dentine-adhesive filling material, is then applied and penetrates the collagen fibre network right into the dental canaliculi. The resulting hybrid layer is cured by light-induced polymerisation. This polymer layer is now micromechanically anchored in the tubules and in the penetrated collagen fibre network by means of tags (pegs).

REFERENCE LIST

1 Root canal filling composition
2 Glass fibre post
3 First end
4 Second end
5 Apical stop
6 Filling material
7 Holder
10 Dentine
11 Dentinal tubules

The invention claimed is:

1. A root canal filling composition for placement in a tooth root canal, the root canal filling composition comprising an elongate glass-fibre post with a first end and a second end, an apical stop which is made of a physiological material and is arranged at the first end, and a filling material, which surrounds the glass-fibre post over its entire surface at least in some regions, wherein the filling material comprises a dentine-adhesive filling material, further wherein the apical stop has a length of not more than 1/10 of the length of the glass-fibre post to thereby allow limiting of cavity formation adjacent the apical stop and allow the tooth to be stabilized by the elongate glass-fibre post adjacent the apical stop.

2. The root canal filling composition according to claim 1, wherein the filling material comprises a composite and/or a self-adhesive material.

3. The root canal filling composition according to claim 1, wherein the glass-fibre post is formed in one or more parts, wherein in the case of a multi-part design a plurality of elongate parts which are not connected to one another in an integrally bonded manner and are arranged next to one another form the glass-fibre post and are detachably connected to one another.

4. The root canal filling composition according to claim 1, wherein the apical stop comprises a physiological material.

5. The root canal filling composition according to claim 1, wherein the apical stop comprises an alkyl cyanoacrylate.

6. The root canal filling composition according to claim 1, wherein the apical stop comprises an alginate, a hyaluronic acid, a collagen, and/or a bone adhesive.

7. The root canal filling composition according to claim 1, wherein the apical stop has a length of not more than 1/20 of the length of the glass-fibre post.

8. A kit for producing a root canal filling composition according to claim 1, containing a glass-fibre post, an apical stop or precursor thereof, and a dentine-adhesive filling material or precursor thereof.

9. The kit according to claim 8, wherein the filling material is premixed and is not cured or is only partially cured.

10. The kit according to claim 8, wherein the filling material is a composite, a dual-curing or light-curing composite and/or a self-adhesive composite.

11. The kit according to claim 8, further comprising a dentine-adhesive primer.

12. The kit according to claim 8, wherein the glass-fibre post, the apical stop or precursor thereof and the dentine-adhesive filling material or precursor thereof are arranged in the kit and present in the form of the root canal filling composition, wherein the filling material arranged on the glass-fibre post is additionally enclosed in an insulated manner in such a way that it is fixed to the glass-fibre post.

13. The kit according to claim 8, wherein the kit comprises each of the components in a quantity to allow the filling of one tooth at a time.

14. A method for applying a root canal filling composition according to claim 1 ex-vivo in a root canal opened beyond the apical region, comprising the following steps in the order given:
   a) placing the physiological apical stop in the root canal, the apical stop optionally protruding from the apical region by being over-tamped, and not extending into the root canal by more than 1/10 of the total root canal length,
   b) applying a filling material in the root canal comprising a glass-fibre post and a dentine-adhesive filling material, and
   c) curing the filling material.

15. The root canal filling composition according to claim 2 wherein the filling material comprises a dual curing composite.

16. The root canal filling composition according to claim 3 wherein in the case of a multi-part design the plurality of elongate parts are detachably connected to one another via a holder.

17. The root canal filling composition according to claim 4 wherein the apical stop comprises a bioresorbable product.

18. The root canal filling composition according to claim 5 wherein the apical stop comprises an alkyl cyanoacrylate with an alkyl chain length in the range of $C_2$-$C_8$.

19. The root canal filling composition according to claim 6 wherein the apical stop comprises a bone adhesive containing at least one of cyanoacrylates, hydroxyapatite, acyl acrylonitrile, dialkyl methylene manolate, α-substituted vinylidene alkylsulphonates, and sulphonates.

20. The kit according to claim 12 wherein the filling material arranged on the glass-fibre post is additionally enclosed in an insulated manner in such a way that it is fixed to the glass-fibre post, in contact to the latter.

21. The kit according to claim 12 wherein the filling material arranged on the glass-fibre post is additionally enclosed in an insulated material in such a way that it is fixed to the glass-fibre post and sealed hermetically and in a sterile manner.

22. The kit according to claim 8, wherein the glass-fibre post, the apical stop or precursor thereof, and the dentine-adhesive filling material or precursor thereof are arranged in the kit spacially separated from each other.

\* \* \* \* \*